(12) United States Patent
Jonczyk et al.

(10) Patent No.: US 6,683,051 B1
(45) Date of Patent: Jan. 27, 2004

(54) PHARMACEUTICAL PREPARATION CONTAINING A CYCLOPEPTIDE AND A CHEMOTHERAPEUTIC AGENT OR AN ANGIOGENESIS INHIBITOR

(75) Inventors: Alfred Jonczyk, Darmstadt (DE); Astrid Perschl, Darmstadt (DE); Simon Goodman, Darmstadt (DE); Sigrid Rösener, Darmstadt (DE); Jutta Haunschild, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/787,374

(22) PCT Filed: Sep. 9, 1999

(86) PCT No.: PCT/EP99/06654

§ 371 (c)(1),
(2), (4) Date: Jun. 4, 2001

(87) PCT Pub. No.: WO00/15244

PCT Pub. Date: Mar. 23, 2000

(30) Foreign Application Priority Data

Sep. 16, 1998 (DE) .......................... 198 42 415

(51) Int. Cl.[7] .............................................. A61K 38/00
(52) U.S. Cl. .......................................................... 514/9
(58) Field of Search ................................ 530/300, 350, 530/382; 514/2, 9

(56) References Cited

FOREIGN PATENT DOCUMENTS

| WO | 9741844 | 11/1997 |
| WO | 9745447 | 12/1997 |
| WO | 9814192 | 4/1998 |
| WO | 9831359 | 7/1998 |

OTHER PUBLICATIONS

Lode HN et al: "Synergy between an antiangiogenic integrin alphav antagonist and an antibody–cytokine fusion protein eradicates spontaneous tumor metastases" Proceedings of the National Academy of Sciences of the United State of America (Feb. 16, 1999) 96(4) 1591–96.

Primary Examiner—Karen Cochrane Carlson
Assistant Examiner—Sheridan Snedden
(74) Attorney, Agent, or Firm—Millen, White, Zelano & Branigan, P.C.

(57) ABSTRACT

The invention relates to a pharmaceutical preparation [lacuna] cyclo(Arg-Gly-Asp-D-Phe-NMe-Val) and/or one of its physiologically acceptable salts and at least one chemotherapeutic agent and/or one of its physiologically acceptable salts and/or an angiogenesis inhibitor and/or one of its physiologically acceptable salts.

14 Claims, No Drawings

PHARMACEUTICAL PREPARATION CONTAINING A CYCLOPEPTIDE AND A CHEMOTHERAPEUTIC AGENT OR AN ANGIOGENESIS INHIBITOR

This application claims the benefit of PCT/EP99/06654, filed Sep. 9, 1999, which claims priority to German application 198 42 415.9, filed Sep. 16, 1998.

The invention relates to a novel pharmaceutical preparation comprising cyclo(Arg-Gly-Asp-D-Phe-NMe-Val) and/or one of its physiologically acceptable salts and at least one chemotherapeutic agent and/or one of its physiologically acceptable salts and/or an angiogenesis inhibitor and/or one of its physiologically acceptable salts.

This novel preparation can be used to control pathologically angiogenic disorders, thromboses, myocardial infarct, coronary heart disease, arteriosclerosis, tumours, osteoporosis, inflammations and infections.

The invention was based on the object of providing novel medicinal products in the form of pharmaceutical preparations which have better properties than known medicinal products used for the same purposes.

This object has been achieved by the finding of the novel preparation.

Cyclo(Arg-Gly-Asp-D-Phe-NMe-Val) is disclosed in EP 0 770 622 and acts in particular as integrin inhibitor, in particular inhibiting the interactions of the $\alpha_v$, $\beta_3$ or $\beta_5$ integrin receptors with ligands, such as, for example, the binding of fibrinogen to the $\alpha_v\beta_3$ integrin receptor. The compound shows particular activity in the case of the integrins $\alpha_v\beta_3$, $\alpha_v\beta_5$, $\alpha_{IIb}\beta_3$ and $\alpha_v\beta_1$, $\alpha_v\beta_6$ and $\alpha_v\beta_8$.

This effect can be detected, for example, by the method described by J. W. Smith et al. in J. Biol. Chem. 265, 12267–12271 (1990).

The present invention is to be regarded as a selection invention in relation to EP 0 770 622.

WO 98/14192 mentions pharmaceutical products which comprise combinations of non-peptide vitronectin receptor antagonists with chemotherapeutic agents. The effect of an antiangiogenesis therapy combined with a chemotherapy is described by J. Folkman in Nature Medicine 1, 27–30 (1995).

The efficacy of cyclo(Arg-Gly-Asp-D-Phe-NMe-Val) in combination with a chemotherapeutic agent can be shown in Lewis lung carcinoma system. The Lewis lung carcinoma is only inadequately influenced by conventional chemotherapeutic agents (Y. Kakeji and B. A. Teicher, Invest. New Drugs 15: 39–48 (1997)). The method for delaying tumour growth is carried out in analogy to Kakeji (F. Mitjans et al., J. Cell Sci. 108: 2825–2838 (1995)).

The invention further relates to a pharmaceutical preparation comprising cyclo(Arg-Gly-Asp-D-Phe-NMe-Val) and/or one of its physiologically acceptable salts and at least one chemotherapeutic agent and/or one of its physiologically acceptable salts.

The invention relates in particular to a pharmaceutical preparation as described, characterized in that a chemotherapeutic agent from a group consisting of
a) alkylating agents,
b) antibiotics,
c) antimetabolites,
d) biologicals and immunomodulators,
e) hormones and antagonists thereof,
f) mustard gas derivatives,
g) alkaloids,
h) inhibitors of matrix metalloproteinases (MMP inhibitors),
i) protein kinase inhibitors,
k) others is employed.

Examples of preferred alkylating agents are busulfan, carboplatin, carmustine, cisplatin, cyclophosphamide, dacarbazine, ifosfamide or lomustine.

Examples of preferred antibiotics are bleomycin, doxorubicin (Adriamycin), idarubicin or plicamycin.

Examples of preferred antimetabolites are sulfonamides or folic acid antagonists such as, for example, also 5-fluorouracil (5-FU), mercaptopurine, methotrexate or thioguanine or 5-FU with calcium folinate (leucovorin).

Examples of preferred biologicals and immunomodulators are interferon a2 A, interleukin2 or levamisole.

Examples of preferred hormones and antagonists thereof are flutamide, goserelin, mitotane or tamoxifen.

Examples of preferred mustard gas derivatives are melphalan, carmustine or nitrogen mustard.

Examples of preferred alkaloids are the taxanes such as docetaxel or paclitaxel, also etoposide, vinblastine or vinovelbine [sic].

Other chemotherapeutic agents mean those which cannot be assigned to the above groups, such as, for example, altretamine, cladribine, gemcitabine, leucovorin, levamisole, pentostatin or irinotecan.

Among inhibitors of matrix metalloproteinases (MMP inhibitors), which are also described, for example, by M. Wittaker [sic] et al. in Current Opinion in Drug Discovery & Development 1, 157–164 (1998), the following compounds are preferred, for example baltimastat (BB-94), marimastat (BB-2516), BB-3644, ilomastat, metastat, AG-3340, BAY-12–9566, AE-941/neovastat, CGS-27023A, RS-113456, RS-130830, Ro-32-3555, Ro-31-9790, CT-1746, CT-1418, D-1927, D-2163.

Protein kinase inhibitors are described, for example, by G. McMahon et al. in Current Opinion in Drug Discovery & Development 1, 131–146 (1998) and by L. M. Strawn et al. in Exp. Opin. Invest. Drugs 7, 553–573 (1998). In the preparations according to the invention, the following receptor tyrosine kinase inhibitors are specifically preferred:

CGP 79787, SU-101 (HWA 486, leflunomide, Arava), SU-5416, SU-5271 (PD-153035), PD-173074, SU-6668, ZD-1839, CP-358774.

The preparations according to the invention also include so-called prodrug derivatives of the angiogenesis inhibitors and/or of the chemotherapeutic agents, i.e. compounds which are modified with, for example, alkyl or acyl groups, sugars or oligopeptides and are rapidly cleaved in the body to give the active compounds according to the invention. The prodrug derivatives include, for example, also the chemotherapeutic agent capecitabine which is the prodrug of 5-FU, as described, for example, in Inpharma No. 1142, 13–14 (1998).

Particular preference is given to a pharmaceutical preparation as described, characterized in that a chemotherapeutic agent from a group consisting of docetaxel, paclitaxel, carboplatin, cisplatin, 5-FU and calcium folinate, irinotecan, cyclophosphamide, carmustine, doxorubicin, vinorelbine, goserelin or gemcitabine is employed.

The use of gemcitabine in tumour treatment is described, for example, by B. J. Braakhuis et al. in Semin-Oncol. 1995 August; 22 (4 Suppl.11): 42–6 or by R. M. Mohammed et al. in Pancreas 1998 January; 16(1): 19–25.

The invention further relates to a pharmaceutical preparation comprising cyclo(Arg-Gly-Asp-D-Phe-NMe-Val) and/or one of its physiologically acceptable salts and gemcitabine and/or one of its physiologically acceptable salts.

The invention further relates to a pharmaceutical preparation comprising cyclo(Arg-Gly-Asp-D-Phe-NMe-Val)

and/or one of its physiologically acceptable salts and at least one angiogenesis inhibitor and/or one of its physiologically acceptable salts.

Preferred angiogenesis inhibitors are described, for example, in Table 1 in WO 9741844.

Particular preference is given to $\alpha_v\beta_3$ and $\alpha_v\beta_5$ integrin inhibitors, for example the compounds mentioned in EP 0 770 622.

The novel pharmaceutical preparation can be produced by converting cyclo(Arg-Gly-Asp-D-Phe-NMe-Val) and/or one of its physiologically acceptable salts and at least one chemotherapeutic agent and/or one of its physiologically acceptable salts and/or an angiogenesis inhibitor and/or one of its physiologically acceptable salts, into a suitable daily dosage form together with at least one solid, liquid or semiliquid excipient or ancillary substance. The preparations obtained in this way can be employed as medicinal products in human or veterinary medicine, in particular for the treatment of tumours. Suitable carrier substances are organic or inorganic substances which are suitable for enteral (for example oral, sublingual or rectal), parenteral or topical (for example transdermal) administration and do not react with the compounds, for example water, vegetable oils, benzyl alcohols, polyethylene glycols, glycerol acetate and other fatty acid glycerides, gelatin, soya lecithin, carbohydrates such as lactose or starch, magnesium stearate, talc, cellulose. Particularly used for oral administration are tablets, coated tablets, capsules, syrups, suspensions or drops, for rectal administration are suppositories, for parenteral administration are solutions, preferably oily or aqueous solutions, also suspensions, emulsions or implants, and for topical administration are ointments, creams or plasters. The active ingredients can also be lyophilized and the resulting lyophilizates be used, for example, for producing injectable products. The preparations can be sterilized and/or contain ancillary substances such as preservatives, stabilizers and/or wetting agents, emulsifiers, salts to influence the osmotic pressure, buffer substances, colours and/or flavours. They may also comprise further active ingredients, for example other substances which lower blood pressure or have a diuretic effect, but also vitamins and/or mineral salts, in particular those which favour metabolic processes.

The preparations according to the invention are used to control pathologically angiogenic disorders, thromboses, myocardial infarct, coronary heart disease, arteriosclerosis, tumours, osteoporosis, inflammations and infections. As a rule, they are employed for controlling tumours, that is to say to inhibit tumour growth or tumour metastases.

It is possible to use cyclo(Arg-Gly-Asp-D-Phe-NMe-Val) in combination products employed for controlling diseases in which a, integrins, especially $\alpha_v\beta_3$ and $\alpha_v\beta_5$, are involved and inhibition thereof forms part of the therapy. In the case of non-oncological disorders, cyclo(Arg-Gly-Asp-D-Phe-NMe-Val) is used in combination with a therapeutic agent typical for this disorder. The pathologies include thrombosis, myocardial infarct, arteriosclerosis, inflammations, stroke, angina pectoris, oncoses, osteolytic diseases such as osteoporosis, pathologically angiogenic diseases such as, for example, inflammations, ophthalmological diseases, diabetic retinopathy, macular degeneration, myopia, ocular histoplasmosis, rheumatoid arthritis, osteoarthritis, rubeotic glaucoma, ulcerative colitis, Crohn's disease, atherosclerosis, psoriasis, restenosis after angioplasty, viral infection, bacterial infection, fungal infection, inflammatory bowel disorders and acute renal failure.

It is possible to use cyclo(Arg-Gly-Asp-D-Phe-NMe-Val) in tumour therapy, also in combination with another angiogenesis inhibitor, a) on surgical removal of a tumour,
b) on radiotherapy,
c) on photodynamic therapy,
d) together with monoclonal antibodies against tumourselective epitopes,
e) together with fusion proteins,
f) together with peptide vaccines and
g) on gene therapy.

The doses of cyclo(Arg-Gly-Asp-D-Phe-NMe-Val) or its salts and of the chemotherapeutic agents and/or the angiogenesis inhibitors are preferably between about 0.1 and 100 mg, in particular between 0.2 and 20 mg, very especially between 0.1 and 10 mg per dose unit. The daily dose is preferably between about 0.001 and 1, in particular between 0.002 and 0.2 mg/kg of body weight.

During chemotherapy, the peptide can be given, for example, also in a dose of 1–10 mg/kg 2 × a week. The chemotherapeutic agents can be administered, for example, also in a dose of 1–10 mg/kg once a week to every 3–4 weeks. However, the specific dose for each patient depends on a wide variety of factors, for example on the efficacy of the specific compound employed, on the age, body weight, general state of health, sex, on the diet, on the time and route of administration, on the excretion rate, drug combination and severity of the particular disorder for which the therapy is applied. Oral administration is preferred.

The invention therefore also relates to the use of the described pharmaceutical preparations for the production of a medicinal product for controlling pathologically angiogenic disorders, thromboses, myocardial infarct, coronary heart disease, arteriosclerosis, tumours, osteoporosis, inflammations and infections.

The invention further relates to the use of the described pharmaceutical preparations for controlling pathologically angiogenic disorders, thromboses, myocardial infarct, coronary heart disease, arteriosclerosis, tumours, osteoporosis, inflammations and infections.

The invention particularly relates to the use of cyclo(Arg-Gly-Asp-D-Phe-NMe-Val) and/or one of its physiologically acceptable salts consecutively or in physical combination with a chemotherapeutic agent and/or one of its physiologically acceptable salts and/or an angiogenesis inhibitor and/or one of its physiologically acceptable salts for producing a medicinal product for controlling tumours.

The invention also relates to the use of cyclo(Arg-Gly-Asp-D-Phe-NMe-Val) and/or one of its physiologically acceptable salts consecutively or in physical combination with a chemotherapeutic agent and/or one of its physiologically acceptable salts for producing a medicinal product for controlling tumours.

The invention furthermore relates to the use of cyclo(Arg-Gly-Asp-D-Phe-NMe-Val) and/or one of its physiologically acceptable salts consecutively or in physical combination with a chemotherapeutic agent and/or one of its physiologically acceptable salts for controlling tumours.

The ingredients of the novel pharmaceutical preparation are preferably administered in combination. However, they can also be administered singly, simultaneously or consecutively.

The invention also relates to a kit consisting of separate packs of
(a) an effective amount of cyclo(Arg-Gly-Asp-D-Phe-NMe-Val) and
(b) an effective amount of a chemotherapeutic agent.

The kit comprises suitable containers such as boxes, individual bottles, bags or ampoules. The kit may, for example, comprise separate ampoules in each of which there is an effective amount of cyclo(Arg-Gly-Asp-D-Phe-NMe-Val) and of the chemotherapeutic agent in dissolved or lyophylized [sic] form.

WO 9814192 discloses various biological tests suitable for determining the concentration of the compounds having a pharmacological effect.

Cyclo(Arg-Gly-Asp-D-Phe-NMe-Val), the therapeutic agent or the angiogenesis inhibitor can if an acidic functionality is present be converted with a base into the relevant acid addition salt, for example by reacting the equivalent amounts of the acid and of the base in an inert solvent such as ethanol and then evaporating.

Bases particularly suitable for this reaction are those which provide physiologically acceptable salts. Thus, an acid can be converted with a base (for example sodium or potassium hydroxide or carbonate) into the corresponding metal, in particular alkali metal or alkaline earth metal, also into the corresponding amount of ammonium salt.

On the other hand, a basic functionality can be converted into the relevant acid addition salt, for example by reacting equivalent amounts of the base and of the acid in an inert solvent such as ethanol and then evaporating. Particularly suitable acids for this reaction are those which provide physiologically acceptable salts. Thus, itris possible to use inorganic acids, for example sulfuric acid, nitric acid, hydrohalic acids such as hydrochloric acid or hydrobromic acid, phosphoric acids such as orthophosphoric acid, sulfamic acid, also organic acids, in particular aliphatic, alicyclic, araliphatic or aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene mono- and disulfonic acids, laurylsulfuric acid. Salts with physiologically unacceptable salts, for example picrates, can be used to isolate and/or purify the compounds of the formula I [sic].

The invention further relates to a pharmaceutical preparation comprising an $\alpha_v\beta_3$ and/or an $\alpha_v\beta_5$ integrin inhibitor and/or one of its physiologically acceptable salts and at least one MMP inhibitor and/or one of its physiologically acceptable salts, and to a pharmaceutical preparation comprising an $\alpha_v\beta_3$ and/or an $\alpha_v\beta_5$ integrin inhibitor and/or one of its physiologically acceptable salts and at least one tyrosin kinase inhibitor and/or one of its physiologically acceptable salts.

Preferred $\alpha_v\beta_3$ and $\alpha_v\beta_5$ integrin inhibitors are described, for example, , in EP 0 770 622, EP 0 710 657, EP 0 820 988, EP 0 820 991, WO 94/12181, WO 94/08577, EP 0 518 586, EO 95/32710, WO 96/00574, WO 96/00730 or in DE 198 50 131.

Among MMP inhibitors and tyrosine kinase inhibitors, those mentioned above are preferred.

EXAMPLE OF TESTING A COMBINATION THERAPY

Delay in tumour growth in analogy to Kakeji (F. Mitjans et al., J. Cell Sci. 108: 2825–2838 (1995)):

Lewis lung carcinoma cells (2× 10E6) are injected into C57BL mice 8–10 weeks old. On the fourth day, cyclo(Arg-Gly-Asp-D-Phe-NMe-Val) (30 mg/kg) is administered i.p. each day [sic]. The tumour growth is measured each day (B. A. Teicher et al., Int. J. Cancer 57: 920–925 (1994)). Once the tumours have reached a particular volume of about 100 mm$^3$, various cytotoxic combination therapies by intraperitoneal injection start on day 7 after tumour inoculation. Examples: 5-fluorouracil (30 mg/kg) or Adriamycin (1.8 mg/kg) are given each day from day 7 to 11. Cyclophosphamide (150 mg/kg), carmustine (15 mg/kg) or gemcitabine (2.5 mg/kg) are given on day 7, 9 and 11. Cisplatin (10 mg/kg) is given on day 7.

The tumours are measured three times a week until a volume of approximately 500 mm$^3$ is reached. The delay in tumour growth is calculated as the time required by an individual tumour to reach 500 mm$^3$ compared with untreated controls.

The following examples relate to pharmaceutical preparations:

Example A

Vials

A solution of 100 g of cyclo(Arg-Gly-Asp-D-Phe-NMe-Val) and/or one of its physiologically acceptable salts, 100 g of the chemotherapeutic agent and 5 g of disodium hydrogenphosphate in 6 l of double-distilled water is adjusted to pH 6.5 with 2N hydrochloric acid, sterilized by filtration, dispensed into vials, lyophilized under sterile conditions and sealed sterile. Each vial contains 5 mg of the active ingredients.

Example B

Suppositories

A mixture of 20 g of cyclo(Arg-Gly-Asp-D-Phe-NMe-Val) and/or one of its physiologically acceptable salts, 20 g of the chemotherapeutic agent is melted with 100 g of soya lecithin and 1400 g of cocoa butter, poured into moulds and left to cool. Each suppository contains 20 mg of active ingredient.

Example C

Solution

A solution is prepared from 1 g of cyclo(Arg-Gly-Asp-D-Phe-NMe-Val) and/or one of its physiologically acceptable salts, 1 g of the chemotherapeutic agent, 9.38 g of NaH$_2$PO$_4$.2H$_2$O, 28.48 g of Na$_2$HPO$_4$.12H$_2$O and 0.1 g of benzalkdnium chloride in 940 ml of double-distilled water. The pH is adjusted to 6.8, the volume is made up to 1 l, and the solution is sterilized by irradiation. This solution can be used in the form of eye drops.

Example D

Ointment 500 mg of cyclo(Arg-Gly-Asp-D-Phe-NMe-Val) and/or one of its physiologically acceptable salts, 500 mg of the chemotherapeutic agent are mixed with 99.5 g of petrolatum under aseptic conditions.

Example E

Tablets

A mixture of 1 kg of cyclo(Arg-Gly-Asp-D-Phe-NMe-Val) and/or one its physiologically acceptable salts, 1 kg of the chemotherapeutic agent, 4 kg of lactose, 1.2 kg of potato starch, 0.2 kg of talc and 0.1 kg of magnesium stearate is compressed to tablets in a conventional way so that each tablet contains 10 mg of active ingredient.

Example F

Coated tablets

Tablets are compressed in analogy to Example E and are then coated in a conventional way with a coating of sucrose, potato starch, talc, tragacanth and colour.

Example G

Capsules 2 kg of *cyclo(Arg-Gly-Asp-D-Phe-NMe-Val) and/or one of its physiologically acceptable salts, 2 kg of the chemotherapeutic agent are packed into hard gelatin capsules in a conventional way so that each capsule contains 20 mg of the active ingredient.

Example H

Ampoules

A solution of 1 kg of cyclo(Arg-Gly-Asp-D-Phe-NMe-Val) and/or one of its physiologically acceptable salts, 1 kg of the chemotherapeutic agent in 60 l of double-distilled water is sterilized by filtration, dispensed into ampoules, lyophilized under sterile conditions and sealed sterile. Each ampoule contains 10 mg of each of the active ingredients.

Example I

Kit

Preparation (kit) for parenteral administration

The preparation contains 500 mg of cyclo(Arg-Gly-Asp-D-Phe-NMe-Val) and/or one of its physiologically acceptable salts and 500 mg of gemcitabine hydrochloride and is produced as follows:

500 mg of each of the two compounds are dissolved in 40 ml of distilled water. The solutions are filtered under sterile conditions and dispensed into 10 ml ampoules and lyophilized.

For intravenous or intramuscular injection, 10 ml of 5% aqueous dextrose are added.

What is claimed is:

1. A pharmaceutical preparation comprising cyclo(Arg-Gly-Asp-D-Phe-NMe-Val) and/or one of the its physiologically acceptable salts and at least one chemotherapeutic agent and/or one of its physiologically acceptable salts and/or an angiogenesis inhibitor and/or one of its physiologically acceptable salts.

2. The pharmaceutical preparation according to claim 1, comprising cyclo(Arg-Gly-Asp-D-Phe-NMe-Val) and/or one of its physiologically acceptable salts and at least one chemotherapeutic agent and/or one of its physiologically acceptable salts.

3. The pharmaceutical preparation according to claim 1, comprising cyclo(Arg-Gly-Asp-D-Phe-NMe-Val) and/or one of its physiologically acceptable salts and at least one angiogenesis inhibitor and/or one of its physiologically acceptable salts.

4. A pharmaceutical preparation according to claim 1, further comprising a chemotherapeutic agent which is
 a) alkylating agents,
 b) antibiotics,
 c) antimetabolites,
 d) biologicals and immunomodulators,
 e) hormones and antagonists thereof,
 f) mustard gas derivatives,
 g) alkaloids
 h) inhibitors of matrix metalloproteinases (MMP inhibitors), or
 i) protein kinase inhibitors.

5. The pharmaceutical preparation according to claim 1, wherein a chemotherapeutic agent which is docetaxel, paclitaxel, carboplatin, cisplatin, 5-FU and calcium folinate, irinotecan, cyclophosphamide, carmustine, doxorubicin, vinorelbine, goserelin or gemcitabine is employed.

6. The pharmaceutical preparation according to claim 1, comprising cyclo(Arg-Gly-Asp-D-Phe-NMe-Val) and/or one of its physiologically acceptable salts and gemcitabine and/or one of its physiologically acceptable salts.

7. The pharmaceutical preparation according to claim 1, wherein an angiogenesis inhibitor which is an $\alpha_v\beta_3$ and $\alpha_v\beta_5$ integrin inhibitor is employed.

8. A process for controlling pathologically angiogenic disorders, thromboses, myocardial infarct, coronary heart diseases, arteriosclerosis, tumors, osteoporosis, inflammations or infections, comprising administering an effective amount of a preparation according to claim 1.

9. A process for controlling pathologically angiogenic disorders, thromboses, myocardial infarct, coronary heart diseases, arteriosclerosis, tumors osteoporosis, inflammations and infections comprising administering a preparation according to claim 2.

10. A process for controlling tumors, comprising administering an effective amount of a preparation according to claim 2.

11. A process for controlling tumors, comprising administering an effective amount of a preparation according to claim 3.

12. A kit comprising separate packs of
 (a) an effective amount of cyclo(Arg-Gly-Asp-D-Phe-NMe-Val) and
 (b) an effective amount of a chemotherapeutic agent.

13. A pharmaceutical preparation comprising an $\alpha_v\beta_3$ and/or $\alpha_v\beta_5$ integrin inhibitor and/or one of its physiologically acceptable salts and at least one MMP inhibitor and/or one of its physiologically acceptable salts, wherein the integrin inhibitor is cyclo(Arg-Gly-Asp-D-Phe-NMe-Val).

14. A pharmaceutical preparation comprising an $\alpha_v\beta_3$ and/or $\alpha_v\beta_5$ integrin inhibitor and/or one of its physiologically acceptable salts and at least one tyrosine kinase inhibitor and/or one of its physiologically acceptable salts, wherein the integrin inhibitor is cyclo(Arg-Gly-Asp-D-Phe-NMe-Val).

* * * * *